(12) United States Patent
Zhang et al.

(10) Patent No.: US 8,071,348 B2
(45) Date of Patent: Dec. 6, 2011

(54) PROTEIN TYROSINE PHOSPHATASE SUBSTRATE-TRAPPING DOUBLE MUTANT AND USES THEREOF

(75) Inventors: Zhong-Yin Zhang, Scarsdale, NY (US); Laiping Xie, Bronx, NY (US); Yan-Ling Zhang, Belmont, MA (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 1257 days.

(21) Appl. No.: 10/340,288

(22) Filed: Jan. 10, 2003

(65) Prior Publication Data
US 2003/0170855 A1 Sep. 11, 2003

Related U.S. Application Data

(60) Provisional application No. 60/347,413, filed on Jan. 14, 2002.

(51) Int. Cl.
*C12N 9/14* (2006.01)
*C12N 5/00* (2006.01)
*C07K 16/40* (2006.01)

(52) U.S. Cl. .................. 435/196; 435/820; 530/389.1; 530/388.26

(58) Field of Classification Search .................. 435/226
See application file for complete search history.

(56) References Cited

U.S. PATENT DOCUMENTS
5,912,138 A 6/1999 Tonks et al.

OTHER PUBLICATIONS

Witkowski et al, Conversion of a beta-ketoacyl synthase to a malonyl decarboxylase by replacement of the active-site cysteine with glutamine. Biochemistry. Sep. 7, 1999;38(36):11643-11650.*
Wishart et al, A single mutation converts a novel phosphotyrosine binding domain into a dual-specificity phosphatase. J Biol Chem. Nov. 10, 1995;270(45):26782-26785.*
Mildvan et al, Quantitative interpretations of double utations of enzymes. Arch Biochem Biophys. May 1, 1992;294(2):327-40. Review. Erratum in: Arch Biochem Biophys Aug. 15, 1992;297(1):18.*
Scapin et al, The structure of apo protein-tyrosine phosphatase 1B C215S mutant: more than just an S—> O change. Protein Sci. Aug. 2001;10(8):1596-605.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Bliska, J.B., et al., "The Yersinia Tyrosine Phosphatase: Specificity of a Bacterial Virulence Determinant for Phosphoproteins in the J774A.1 Macrophage"; J. Exp. Med., Dec. 1992, pp. 1625-1630, vol. 176.
Flint, A.J., et al., "Development of 'substrate-trapping' mutants to identify physiological substrates of protein tyrosine phosphatases"; Proc. Natl. Acad. Sci. USA, Mar. 1997, pp. 1680-1685, vol. 94.
Garton, A.J., et al., "Identification of p130cas as a Substrate for the Cytosolic Protein Tyrosine Phosphatase PTP-PEST"; Molecular and Cellular Biology, Nov. 1996, pp. 6408-6418, vol. 16, No. 11.
Liu, F., et al., "Direct Binding of the Proline-rich Region of Protein Tyrosine Phosphatase 1B to the Src Homology 3 Domain of p130Cas"; The Journal of Biological Chemistry, Dec. 6, 1996, pp. 31290-3195, vol. 271, No. 49.
Milarski, K.L., et al., "Sequence Specificity in Recognition of the Epidermal Growth Factor Receptor by Protein Tyrosine Phosphatase 1B"; The Journal of Biological Chemistry, Nov. 5, 1993, pp. 23634-23639, vol. 268, No. 31.
Sarmiento, M., et al., "Molecular Basis for Substrate Specificity of Protein-tyrosine Phosphatase 1B"; The Journal of Biological Chemistry, Oct. 9, 1998, pp. 26368-26374, vol. 273, No. 41.
Scapin, G., et al., "The structure of apo protein-tyrosine phosphatase 1B C215S mutant: More than just and S —> O change"; Protein Science, 2001, pp. 1596-1605, vol. 10.
Sun, H., et al., "MKP-1 (3CH134), an Immediate Early Gene Product, Is a Dual Specificity Phosphatase That Dephosphorylates MAP Kinase In Vivo"; Cell, Nov. 5, 1993, pp. 487-93, vol. 75.
Zhang, et al., "Thermodynamic Study of Ligand Binding to Protein-tyrosine Phosphatase 1B and Its Substrate-trapping Mutants"; The Journal of Biological Chemistry, Nov. 3, 2000, pp. 34205-34212, vol. 275, No. 44.

* cited by examiner

*Primary Examiner* — Sheridan Swope
(74) *Attorney, Agent, or Firm* — Amster, Rothstein & Ebenstein LLP

(57) ABSTRACT

The present invention provides protein tyrosine phosphatases (PTP) in which the invariant aspartate residue and the invariant glutamine residue are each replaced with a replacement amino acid residue, wherein the replacement residues together cause a reduction in catalytic rate ($k_{cat}$) of the enzyme and an increase in substrate-binding affinity ($K_d$) of the enzyme. The present invention further provides methods for identifying a substrate of a PTP. Also provided are kits for identifying a substrate of a PTP. Additionally, the present invention provides methods for identifying an agent that alters interaction between a PTP and a substrate of the PTP. The invention also provides methods for reducing the activity of a substrate of a PTP.

3 Claims, 5 Drawing Sheets

FIG. 2

|  |  | 262 | SEQ ID NO |
|---|---|---|---|
| PTP1B | VLLEMRKFRM | GLIQTADQLR | 3 |
| TcPTP | VLLNMRKYRM | GLIQTPDQLR | 4 |
| HDPTP | LVRRMRQQRK | HMLQEKLHLR | 5 |
| SHPTP1 | TIQMVRAQRS | GMVQTEAQYK | 6 |
| SHPTP2 | TIQMVRSQRS | GMVQTEAQYR | 7 |
| PTP-PEST | LIQEMRTQRH | SAVQTKEQYE | 8 |
| PTP-MEG1 | IVRTMRDQRA | MMIQTPSQYR | 9 |
| PTP-MEG2 | TVSRMRTQRA | FSIQTPEQYY | 10 |
| PTPH1 | IVRKMRDQRA | MMVQTSSQYK | 11 |
| GLEPP1 | LVSEMRSYRM | SMVQTEEQYI | 12 |
| BDP1 | VVLKMRKQRP | AAVQTEEQYR | 13 |
| HePTP | IVCQLRLDRG | GMIQTDEQYQ | 14 |
| STEP | TTCQLRQDRG | GMIQHCEQYQ | 15 |
| PCPTP1 | IVQCLRMDRG | GMVQTSEQYE | 16 |
| PTPD1 | VLDMLRQQRM | MLVQTLCQYT | 17 |
| PTPD2 | MLRLLREQRM | FMIQTIAQYK | 18 |
| PTPBAS | LVRCMRLQRH | GMVQTEDQYI | 19 |
| CD45 | YVVKLRRQRC | LMVQVEAQYI | 20 |
| LAR | HVTCMRSQRN | YMVQTEDQYV | 21 |
| PTPα | FVSRIRAQRC | QMVQTDMQYV | 22 |
| PTPβ | AVHDLRLHRV | HMVQTECQYV | 23 |
| PTPγ | FLKHIRTQRN | YLVQTEEQYI | 24 |
| PTPδ | HVTLMRAQRN | YMVQTEDQYI | 25 |
| PTPε | FVSRIRNQRP | QMVQTDMQYT | 26 |
| PTPζ | FLKHIRSQRN | YLVQTEEQYV | 27 |
| PTPσ | HVTLMRSQRN | YMVQTEDQYS | 28 |
| PTPρ | CVRELRAQRV | NLVQTEEQYV | 29 |
| PTPκ | CVKALRSRRI | NMVQTEEQYI | 30 |
| PTPμ | CVRELRSRRV | NMVQTEEQYV | 31 |
| PTPλ | CVKTLCSRRV | NMIQTEEQYI | 32 |
| DEP-1 | IVYDLRMHRP | LMVQTEDQYV | 33 |
| SAP-1 | FVRKMRESRP | LMVQTEAQYV | 34 |
| yPTP1 | IVLQLRSQRM | KMVQTKDQFL | 35 |
| yPTP2 | IVNELRKQRI | SMVQNLTQYI | 36 |
| YOP51 | MVSQMRVQRNGIMVQKDEQLD | | 37 |

SEQUENCE LISTING

<160> NUMBER OF SEQ ID NOS: 37

<210> SEQ ID NO 1
<211> LENGTH: 9
<212> TYPE: PRT
<213> ORGANISM: Artificial
<220> FEATURE:
<223> OTHER INFORMATION: consensus
<220> FEATURE:
<221> NAME/KEY: MISC_FEATURE
<222> LOCATION: (1)..(1)
<223> OTHER INFORMATION: X of position 1 can be H (histidine) or V
      (valine)
<220> FEATURE:
<221> NAME/KEY: MISC_FEATURE
<222> LOCATION: (3)..(7)
<223> OTHER INFORMATION: X of positions 3-7 can be any amino acid
<220> FEATURE:
<221> NAME/KEY: MISC_FEATURE
<222> LOCATION: (9)..(9)
<223> OTHER INFORMATION: X of position 9 can be S (serine) or T
      (threonine)

<400> SEQUENCE: 1

Xaa Cys Xaa Xaa Xaa Xaa Xaa Arg Xaa
1               5

<210> SEQ ID NO 2
<211> LENGTH: 11
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: X of position 5 is phosphotyrosine

<400> SEQUENCE: 2

Asp Ala Asp Glu Xaa Leu Ile Pro Gln Gln Gly
1               5                   10

<210> SEQ ID NO 3
<211> LENGTH: 20
<212> TYPE: PRT
<213> ORGANISM: Homo sapiens

<400> SEQUENCE: 3

Val Leu Leu Glu Met Arg Lys Phe Arg Met Gly Leu Ile Gln Thr Ala
1               5                   10                  15

Asp Gln Leu Arg
            20

<210> SEQ ID NO 4
<211> LENGTH: 20
<212> TYPE: PRT
<213> ORGANISM: Homo sapiens

<400> SEQUENCE: 4

Val Leu Leu Asn Met Arg Lys Tyr Arg Met Gly Leu Ile Gln Thr Pro
1               5                   10                  15

Asp Gln Leu Arg
            20

<210> SEQ ID NO 5
<211> LENGTH: 20
<212> TYPE: PRT
<213> ORGANISM: Homo sapiens

```
<400> SEQUENCE: 5

Leu Val Arg Arg Met Arg Gln Gln Arg Lys His Met Leu Gln Glu Lys
1               5                   10                  15

Leu His Leu Arg
            20

<210> SEQ ID NO 6
<211> LENGTH: 20
<212> TYPE: PRT
<213> ORGANISM: Homo sapiens

<400> SEQUENCE: 6

Thr Ile Gln Met Val Arg Ala Gln Arg Ser Gly Met Val Gln Thr Glu
1               5                   10                  15

Ala Gln Tyr Lys
            20

<210> SEQ ID NO 7
<211> LENGTH: 20
<212> TYPE: PRT
<213> ORGANISM: Homo sapiens

<400> SEQUENCE: 7

Thr Ile Gln Met Val Arg Ser Gln Arg Ser Gly Met Val Gln Thr Glu
1               5                   10                  15

Ala Gln Tyr Arg
            20

<210> SEQ ID NO 8
<211> LENGTH: 20
<212> TYPE: PRT
<213> ORGANISM: Homo sapiens

<400> SEQUENCE: 8

Leu Ile Gln Glu Met Arg Thr Gln Arg His Ser Ala Val Gln Thr Lys
1               5                   10                  15

Glu Gln Tyr Glu
            20

<210> SEQ ID NO 9
<211> LENGTH: 20
<212> TYPE: PRT
<213> ORGANISM: Homo sapiens

<400> SEQUENCE: 9

Ile Val Arg Thr Met Arg Asp Gln Arg Ala Met Met Ile Gln Thr Pro
1               5                   10                  15

Ser Gln Tyr Arg
            20

<210> SEQ ID NO 10
<211> LENGTH: 20
<212> TYPE: PRT
<213> ORGANISM: Homo sapiens

<400> SEQUENCE: 10

Thr Val Ser Arg Met Arg Thr Gln Arg Ala Phe Ser Ile Gln Thr Pro
1               5                   10                  15

Glu Gln Tyr Tyr
            20

<210> SEQ ID NO 11
```

```
<211> LENGTH: 20
<212> TYPE: PRT
<213> ORGANISM: Homo sapiens

<400> SEQUENCE: 11

Ile Val Arg Lys Met Arg Asp Gln Arg Ala Met Met Val Gln Thr Ser
1               5                   10                  15

Ser Gln Tyr Lys
            20

<210> SEQ ID NO 12
<211> LENGTH: 20
<212> TYPE: PRT
<213> ORGANISM: Homo sapiens

<400> SEQUENCE: 12

Leu Val Ser Glu Met Arg Ser Tyr Arg Met Ser Met Val Gln Thr Glu
1               5                   10                  15

Glu Gln Tyr Ile
            20

<210> SEQ ID NO 13
<211> LENGTH: 20
<212> TYPE: PRT
<213> ORGANISM: Homo sapiens

<400> SEQUENCE: 13

Val Val Leu Lys Met Arg Lys Gln Arg Pro Ala Ala Val Gln Thr Glu
1               5                   10                  15

Glu Gln Tyr Arg
            20

<210> SEQ ID NO 14
<211> LENGTH: 20
<212> TYPE: PRT
<213> ORGANISM: Homo sapiens

<400> SEQUENCE: 14

Ile Val Cys Gln Leu Arg Leu Asp Arg Gly Gly Met Ile Gln Thr Asp
1               5                   10                  15

Glu Gln Tyr Gln
            20

<210> SEQ ID NO 15
<211> LENGTH: 20
<212> TYPE: PRT
<213> ORGANISM: Homo sapiens

<400> SEQUENCE: 15

Thr Thr Cys Gln Leu Arg Gln Asp Arg Gly Gly Met Ile Gln His Cys
1               5                   10                  15

Glu Gln Tyr Gln
            20

<210> SEQ ID NO 16
<211> LENGTH: 20
<212> TYPE: PRT
<213> ORGANISM: Homo sapiens

<400> SEQUENCE: 16

Ile Val Gln Cys Leu Arg Met Asp Arg Gly Gly Met Val Gln Thr Ser
1               5                   10                  15

Glu Gln Tyr Glu
```

-continued

```
                    20

<210> SEQ ID NO 17
<211> LENGTH: 20
<212> TYPE: PRT
<213> ORGANISM: Homo sapiens

<400> SEQUENCE: 17

Val Leu Asp Met Leu Arg Gln Gln Arg Met Met Leu Val Gln Thr Leu
1               5                   10                  15

Cys Gln Tyr Thr
            20

<210> SEQ ID NO 18
<211> LENGTH: 20
<212> TYPE: PRT
<213> ORGANISM: Homo sapiens

<400> SEQUENCE: 18

Met Leu Arg Leu Leu Arg Glu Gln Arg Met Phe Met Ile Gln Thr Ile
1               5                   10                  15

Ala Gln Tyr Lys
            20

<210> SEQ ID NO 19
<211> LENGTH: 20
<212> TYPE: PRT
<213> ORGANISM: Homo sapiens

<400> SEQUENCE: 19

Leu Val Arg Cys Met Arg Leu Gln Arg His Gly Met Val Gln Thr Glu
1               5                   10                  15

Asp Gln Tyr Ile
            20

<210> SEQ ID NO 20
<211> LENGTH: 20
<212> TYPE: PRT
<213> ORGANISM: Homo sapiens

<400> SEQUENCE: 20

Tyr Val Val Lys Leu Arg Arg Gln Arg Cys Leu Met Val Gln Val Glu
1               5                   10                  15

Ala Gln Tyr Ile
            20

<210> SEQ ID NO 21
<211> LENGTH: 20
<212> TYPE: PRT
<213> ORGANISM: Homo sapiens

<400> SEQUENCE: 21

His Val Thr Cys Met Arg Ser Gln Arg Asn Tyr Met Val Gln Thr Glu
1               5                   10                  15

Asp Gln Tyr Val
            20

<210> SEQ ID NO 22
<211> LENGTH: 20
<212> TYPE: PRT
<213> ORGANISM: Homo sapiens

<400> SEQUENCE: 22
```

```
Phe Val Ser Arg Ile Arg Ala Gln Arg Cys Gln Met Val Gln Thr Asp
1               5                   10                  15

Met Gln Tyr Val
            20

<210> SEQ ID NO 23
<211> LENGTH: 20
<212> TYPE: PRT
<213> ORGANISM: Homo sapiens

<400> SEQUENCE: 23

Ala Val His Asp Leu Arg Leu His Arg Val His Met Val Gln Thr Glu
1               5                   10                  15

Cys Gln Tyr Val
            20

<210> SEQ ID NO 24
<211> LENGTH: 20
<212> TYPE: PRT
<213> ORGANISM: Homo sapiens

<400> SEQUENCE: 24

Phe Leu Lys His Ile Arg Thr Gln Arg Asn Tyr Leu Val Gln Thr Glu
1               5                   10                  15

Glu Gln Tyr Ile
            20

<210> SEQ ID NO 25
<211> LENGTH: 20
<212> TYPE: PRT
<213> ORGANISM: Homo sapiens

<400> SEQUENCE: 25

His Val Thr Leu Met Arg Ala Gln Arg Asn Tyr Met Val Gln Thr Glu
1               5                   10                  15

Asp Gln Tyr Ile
            20

<210> SEQ ID NO 26
<211> LENGTH: 20
<212> TYPE: PRT
<213> ORGANISM: Homo sapiens

<400> SEQUENCE: 26

Phe Val Ser Arg Ile Arg Asn Gln Arg Pro Gln Met Val Gln Thr Asp
1               5                   10                  15

Met Gln Tyr Thr
            20

<210> SEQ ID NO 27
<211> LENGTH: 20
<212> TYPE: PRT
<213> ORGANISM: Homo sapiens

<400> SEQUENCE: 27

Phe Leu Lys His Ile Arg Ser Gln Arg Asn Tyr Leu Val Gln Thr Glu
1               5                   10                  15

Glu Gln Tyr Val
            20

<210> SEQ ID NO 28
<211> LENGTH: 20
<212> TYPE: PRT
```

-continued

<213> ORGANISM: Homo sapiens

<400> SEQUENCE: 28

His Val Thr Leu Met Arg Ser Gln Arg Asn Tyr Met Val Gln Thr Glu
1               5                   10                  15

Asp Gln Tyr Ser
            20

<210> SEQ ID NO 29
<211> LENGTH: 20
<212> TYPE: PRT
<213> ORGANISM: Homo sapiens

<400> SEQUENCE: 29

Cys Val Arg Glu Leu Arg Ala Gln Arg Val Asn Leu Val Gln Thr Glu
1               5                   10                  15

Glu Gln Tyr Val
            20

<210> SEQ ID NO 30
<211> LENGTH: 20
<212> TYPE: PRT
<213> ORGANISM: Homo sapiens

<400> SEQUENCE: 30

Cys Val Lys Ala Leu Arg Ser Arg Arg Ile Asn Met Val Gln Thr Glu
1               5                   10                  15

Glu Gln Tyr Ile
            20

<210> SEQ ID NO 31
<211> LENGTH: 20
<212> TYPE: PRT
<213> ORGANISM: Homo sapiens

<400> SEQUENCE: 31

Cys Val Arg Glu Leu Arg Ser Arg Arg Val Asn Met Val Gln Thr Glu
1               5                   10                  15

Glu Gln Tyr Val
            20

<210> SEQ ID NO 32
<211> LENGTH: 20
<212> TYPE: PRT
<213> ORGANISM: Homo sapiens

<400> SEQUENCE: 32

Cys Val Lys Thr Leu Cys Ser Arg Arg Val Asn Met Ile Gln Thr Glu
1               5                   10                  15

Glu Gln Tyr Ile
            20

<210> SEQ ID NO 33
<211> LENGTH: 20
<212> TYPE: PRT
<213> ORGANISM: Homo sapiens

<400> SEQUENCE: 33

Ile Val Tyr Asp Leu Arg Met His Arg Pro Leu Met Val Gln Thr Glu
1               5                   10                  15

Asp Gln Tyr Val
            20

```
<210> SEQ ID NO 34
<211> LENGTH: 20
<212> TYPE: PRT
<213> ORGANISM: Homo sapiens

<400> SEQUENCE: 34

Phe Val Arg Lys Met Arg Glu Ser Arg Pro Leu Met Val Gln Thr Glu
1               5                   10                  15

Ala Gln Tyr Val
            20

<210> SEQ ID NO 35
<211> LENGTH: 20
<212> TYPE: PRT
<213> ORGANISM: Saccharomyces cerevisiae

<400> SEQUENCE: 35

Ile Val Leu Gln Leu Arg Ser Gln Arg Met Lys Met Val Gln Thr Lys
1               5                   10                  15

Asp Gln Phe Leu
            20

<210> SEQ ID NO 36
<211> LENGTH: 20
<212> TYPE: PRT
<213> ORGANISM: Saccharomyces cerevisiae

<400> SEQUENCE: 36

Ile Val Asn Glu Leu Arg Lys Gln Arg Ile Ser Met Val Gln Asn Leu
1               5                   10                  15

Thr Gln Tyr Ile
            20

<210> SEQ ID NO 37
<211> LENGTH: 21
<212> TYPE: PRT
<213> ORGANISM: Yersinia enterocolitica

<400> SEQUENCE: 37

Met Val Ser Gln Met Arg Val Gln Arg Asn Gly Ile Met Val Gln Lys
1               5                   10                  15

Asp Glu Gln Leu Asp
            20
```

PROTEIN TYROSINE PHOSPHATASE SUBSTRATE-TRAPPING DOUBLE MUTANT AND USES THEREOF

CROSS-REFERENCE TO RELATED APPLICATION

This application claims the benefit of U.S. Provisional Application 60/347,413, filed Jan. 14, 2002.

STATEMENT OF GOVERNMENT INTEREST

This invention was made with government support under NIH Grant No. GM55242. As such, the United States government has certain rights in this invention.

BACKGROUND OF THE INVENTION

Sequencing of the human and other genomes has radically changed the ways in which we identify and characterize genes. Typically, database searches that are based on structural similarities can assign a gene product to an established protein family. Although members of protein families often share a common mechanism of action, the cellular processes in which they are involved can be both highly specialized and fundamentally important.

Protein tyrosine phosphatases (PTPs), enzymes which have conserved catalytic domains but are involved in controlling a broad constellation of cellular processes (1-3), provide a striking example of conserved structures associated with functional diversity. The hallmark that defines the PTP superfamily is the active site amino acid sequence (H/V)C(X)$_5$R(S/T) (SEQ ID NO:1), also referred to as the PTP signature motif, within the catalytic domain. To date, analysis of the nearly completed human genome has revealed 112 predicted human PTPs (4). Therefore, it is relatively easy to attribute a general role to a PTP gene product based upon structural homologies. However, determination of the exact physiological function of a PTP requires a tedious and protracted effort. Identification of the cellular substrates of individual PTPs will help to elucidate the biological functions of individual PTPs. A major challenge, though, is the development of technologies for rapid substrate identification that can be applied to the entire PTP family.

Detailed mechanistic studies have shown that PTPs utilize a common mechanism for phosphomonoester hydrolysis (5). See FIG. 1. The PTPs employ the active site cysteine (e.g., Cys215 in PTP1B) as the attacking nucleophile, thereby forming a thiophosphoryl enzyme intermediate ("E-P") (6, 7). The E-P formation is assisted by a conserved aspartic acid (e.g., Asp181 in PTP1B), functioning as a general acid, to neutralize the build-up of a negative charge on the leaving group (8, 9). For the hydrolysis of E-P, Asp181, previously functioning as a general acid in E-P formation, acts as a general base, abstracting a proton from the attacking water (10, 11). This enhances the rate of E-P hydrolysis, thereby regenerating the active enzyme. The PTPs further accelerate the formation and hydrolysis of E-P by preferentially binding the pentacoordinated transition states with the guanidinium side chain of the active site arginine residue (e.g., Arg221 in PTP1B) (12, 13).

Because of the transient nature of the enzyme•substrate complex, it has been difficult to isolate substrates with wild-type PTPs. Based upon insights from mechanistic studies, two types of "substrate-trapping" mutant PTPs have been developed. In the first, the active site Cys residue is replaced by a Ser (14-16); in the second, the general acid Asp residue is substituted by an Ala (17, 18; see U.S. Pat. Nos. 5,912,138 and 5,951,979). These mutants retain the ability to bind substrates; however, because they are either unable to carry out substrate dephosphorylation (the Cys-to-Ser mutant) or severely impaired in carrying out substrate dephosphorylation (the Asp-to-Ala mutant), capture of the PTP enzyme•substrate complex becomes possible.

The substrate-trapping mutant PTPs have been used as affinity reagents to isolate and identify physiological substrates for various PTPs. Nevertheless, to date, only a limited number of PTP substrates have been identified by the substrate-trapping approach, and these have been mostly abundant proteins. For example, the adapter protein p130 has been found to be the target of several PTPs, including PTP1B (19), PTP-PEST (17), the *Yersinia* PTP (20), PTPα (21), LAR (22), and SAP (23). The fact that only a few proteins have been identified as PTP substrates is surprising, given the large number of protein tyrosine kinases and phosphotyrosine-(pTyr-) containing proteins in the cell. One possible explanation may be that the affinity of the available trapping mutants is not sufficiently high, such that only heavily populated phosphoproteins can be isolated. Accordingly, in view of the foregoing, there exists a need to create an improved PTP substrate-trapping mutant, with a higher affinity, that will enable the identification of less abundant substrates.

SUMMARY OF THE INVENTION

The inventors describe herein the design and characterization of a novel protein tyrosine phosphatase 1B (PTP1B) substrate-trapping double mutant (PTP1B/D181A/Q262A) that displays 6- and 28-fold higher affinity than the existing D181A and C215S mutants, respectively. Because both Asp181 and Gln262 are invariant among PTPs, this double mutant should be appropriate for substrate identification for all members of the PTP family. Identification and characterization of specific PTP/substrate interactions will permit the association of functions with individual PTPs, and implicate specific PTPs to specific signaling pathways.

Accordingly, the present invention provides protein tyrosine phosphatases (PTP) in which the invariant aspartate residue and the invariant glutamine residue are each replaced with a replacement amino acid residue, wherein the replacement residues together cause a reduction in catalytic rate ($k_{cat}$) of the enzyme and an increase in substrate-binding affinity ($K_d$) of the enzyme.

The present invention also provides methods for identifying a substrate of PTPs by (a) contacting a candidate substrate with at least one PTP in which the invariant aspartate residue and the invariant glutamine residue are each replaced with a replacement amino acid residue, wherein the replacement residues together cause a reduction in catalytic rate ($k_{cat}$) of the enzyme and an increase in substrate-binding affinity ($K_d$) of the enzyme; and (b) assessing the ability of the candidate agent to bind to the PTP.

Further provided are kits for identifying a substrate of a PTP, comprising: (a) at least one PTP in which the invariant aspartate residue and the invariant glutamine residue are each replaced with a replacement amino acid residue, wherein the replacement residues together cause a reduction in catalytic rate ($k_{cat}$) of the enzyme and an increase in substrate-binding affinity ($K_d$) of the enzyme; and (b) reagents suitable for detecting binding of the PTP to a candidate substrate.

Finally, the present invention provides methods for identifying an agent that alters interaction between a PTP and a substrate of the PTP by (a) identifying a substrate of a PTP in accordance with the previously described method; (b) contacting the PTP and the substrate, in the presence of a candidate agent; and (c) assessing the ability of the candidate agent to inhibit PTP-substrate interaction.

Additional objects of the present invention will be apparent in view of the description which follows.

BRIEF DESCRIPTION OF THE FIGURES

FIG. 2 depicts an amino acid sequence alignment of 32 human PTPs, two yeast PTPs, and the *Yersinia* PTP YOP51, surrounding Gln262 in PTP1B. Conserved residues are shown in bold.

DETAILED DESCRIPTION OF THE INVENTION

Figure 1:
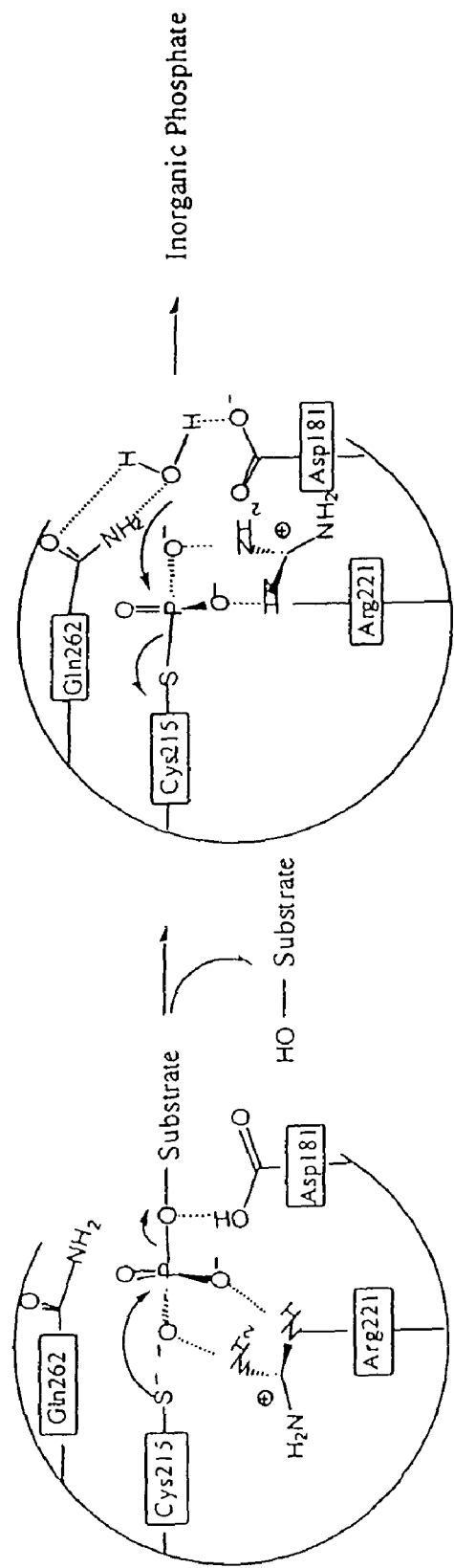
FIG. 1 illustrates a chemical mechanism for the PTP1B-catalyzed dephosphorylation reaction.

The present invention provides mutant protein tyrosine phosphatases (PTP) having reduced or no catalytic activity relative to the wild-type PTP. The term "mutant" is used herein to refer to a gene or its gene product which exhibits at least one modification in its sequence or its functional properties as compared with the wild-type gene or its gene product. In contrast, the term "wild-type" refers to the characteristic genotype (or phenotype) for a particular gene (or its gene product), as found most frequently in its natural source (e.g., in a natural population). A wild-type animal, for example, expresses a functional PTP. Because the substrate-trapping PTP mutant of the present invention retains the ability to bind tyrosine phosphorylated substrates of the wild-type PTP, it is useful in binding, or trapping, one or more substrates of the PTP.

In the mutant PTPs of the present invention, the invariant aspartate residue is replaced with a replacement amino acid residue, and the invariant glutamine residue is replaced with a replacement amino acid residue. As used herein, the term "invariant residue" refers to an amino acid residue that is conserved within a particular family of proteins or enzymes. For example, in PTP1B, both Asp181 and Gln262 are invariant among other members of the PTP family. The invariant aspartate and glutamine residues may be identified in any other PTP by aligning the PTP nucleotide or amino acid sequence with that of PTP1B or another PTP for which the locations of the invariant aspartate and glutamine residues is known (see, e.g., FIG. 2). The replacement amino acids in the PTP enzyme of the present invention may be any amino acids that naturally occur. Examples of replacement amino acid residues include, without limitation, alanine, arginine, asparagine, cysteine, glutamine, glycine, histidine, isoleucine, leucine, lysine, methionine, phenylalanine, proline, serine, threonine, tryptophan, tyrosine, and valine. Preferably, the replacement amino acid residue is one with an aliphatic R group, e.g., isoleucine, valine or leucine. In the most preferred embodiments, the invariant aspartate and glutamine residues are replaced with alanine residues (see Experimental Details).

Examples of methods that may be employed in the synthesis of the PTP, and a mutant version of this sequence containing the replacement amino acid residues of the present invention, include, but are not limited to, solid-phase peptide synthesis, solution-method peptide synthesis, and synthesis using any of the commercially-available peptide synthesizers. The double mutant PTP of the present invention may contain coupling agents and protecting groups, which are used in the synthesis of protein sequences, and which are well-known to one of skill in the art.

The double mutant PTP of the present invention also may be produced from a PTP-encoding deoxyribonucleic acid (DNA) that has been mutated using methods known to one of skill in the art. These methods of DNA mutation include, but are not limited to, chemical mutagenesis, disruption (e.g., by allelic exchange), illegitimate recombination, PCR-mediated mutagenesis, signature-tagged mutagenesis, site-directed mutagenesis, targeted gene disruption, and transposon mutagenesis. Preferably, the method of mutation of the present invention is PCR-mediated mutagenesis.

The replacement amino acid residues in the PTPs of the present invention collectively bring about a reduction in the PTP's catalytic activity relative to the catalytic activity of the wild-type PTP. Specifically, the replacement residues together cause a reduction in catalytic rate ($k_{cat}$) of the enzyme. In some embodiments of the present invention, the $k_{cat}$ of the PTP is reduced by at least 100-fold. In other embodiments of the present invention, the $k_d$ of the PTP is reduced by at least 1,000-fold.

The mutant PTPs of the present invention, which contains the replacement amino acid residues, do not lose their ability to bind tyrosine phosphorylated substrates of the wild-type PTP. In fact, the replacement amino acid residues in the PTPs of the present invention collectively bring about an increase in the PTP's binding ability relative to the binding ability of the wild-type PTP enzyme. Specifically, the replacement residues together cause an increase in substrate-binding affinity ($K_d$) of the enzyme. In some embodiments of the present invention, the $K_d$ of the PTP is increased by at least 10-fold. In other embodiments of the present invention, the $K_d$ of the PTP enzyme is increased by at least 30-fold.

The PTPs of the present invention may be any member of the PTP family, either prokaryotic (e.g., YOP51) or eukaryotic (e.g., from yeast or mammals, including humans), now known or later discovered. Examples of PTPs include, without limitation, any of the PTPs listed in FIG. 2. Preferred PTPs include PTP1B, PTP-PEST, PTPγ, TcPTP, DEP-1, PTPµ, LAR, CD45, PTPH1, PTPα, SHP1, SHP2, PTP-MEG1, PTPβ, HePTP, SAP-1, and YOP51. In particularly preferred embodiments, the PTP is PTP1B. Unless otherwise indicated, "PTP1B" includes both a PTP1B protein and a "PTP1B analogue". A "PTP1B analogue" is a functional variant of the PTP1B peptide, having PTP1B biological activity, that has 60% or greater (preferably, 70% or greater) amino-acid-sequence homology with the PTP1B protein, as well as a fragment of the PTB1B protein having PTP1B biological activity. As further used herein, the term "PTP1B biological activity" refers to the activity of a protein or peptide that hydrolyzes phosphomonoesters, as described herein. Additionally, unless otherwise indicated, "protein" shall include a protein, protein domain, polypeptide, or peptide.

In some embodiments of the invention, the PTP is PTP1B, and the invariant aspartate residue is located at position 181 of the PTP1B amino acid sequence. In other embodiments, the PTP is PTP1B, and the invariant glutamine residue is located at position 262 of the PTP1B amino acid sequence. In further embodiments of the present invention, the PTP is PTP1B, the invariant aspartate residue is located at position 181 of the PTP1B amino acid sequence, and the invariant glutamine residue is located at position 262 of the PTP1B amino acid sequence. As described herein, this PTP1B substrate-trapping double mutant, PTP1B/D181A/Q262A, displays 6- and 28-fold higher affinity than the existing D181A and C215S mutants, respectively. See Experimental Details.

The present invention is also directed to methods for identifying a substrate of a PTP. The methods comprise the steps of: (a) contacting a candidate substrate with at least one PTP in which the invariant aspartate residue and the invariant glutamine residue are each replaced with a replacement amino acid residue, wherein the replacement residues together cause a reduction in catalytic rate ($k_{cat}$) of the enzyme and an increase in substrate-binding affinity ($K_d$) of the enzyme; and (b) assessing the ability of the candidate agent to bind to the PTP. Also provided is a substrate identified by the method of the present invention.

In these methods, the PTP may be any member of the PTP family, as previously discussed in relation to the mutants of the invention.

In these methods, the invariant aspartate residue of the PTP is replaced with a replacement amino acid residue, and the invariant glutamine residue is replaced with a replacement amino acid residue. The replacement amino acids in the PTP may be any amino acids that naturally occur, as previously discussed.

In some embodiments of these methods, the invariant aspartate residue is replaced with an alanine residue. In other embodiments, the invariant aspartate residue is replaced with an alanine residue. In preferred embodiments, the invariant aspartate residue is replaced with an alanine residue, and the invariant glutamine residue is replaced with an alanine residue.

In these methods, the replacement amino acid residues in the PTP collectively bring about a reduction in the PTP's catalytic activity relative to the catalytic activity of the wild-type PTP. Specifically, the replacement residues together cause a reduction in catalytic rate ($k_{cat}$) of the enzyme. In some embodiments of these methods, the $k_{cat}$ of the PTP is reduced by at least 100-fold. In other embodiments, the $k_{cat}$ of the PTP is reduced by at least 1,000-fold. Moreover, the replacement amino acid residues in the PTP collectively bring about an increase in the PTP's binding ability relative to the binding ability of the wild-type PTP. Specifically, the replacement residues together cause an increase in substrate-binding affinity ($K_d$) of the enzyme. In some embodiments of the present invention, the $K_d$ of the PTP is increased by at least 10-fold. In other embodiments of the present invention, the $K_d$ of the PTP is increased by at least 30-fold.

In some embodiments of these methods, the PTP is PTP1B, and the invariant aspartate residue is located at position 181 of the PTP1B amino acid sequence. In other embodiments, the PTP of the present invention is PTP1B, and the invariant glutamine residue is located at position 262 of the PTP1B amino acid sequence. In further embodiments, the PTP is PTP1B, the invariant aspartate residue is located at position 181 of the PTP1B amino acid sequence, and the invariant glutamine residue is located at position 262 of the PTP1B amino acid sequence. This PTP1B substrate-trapping double mutant may be referred to as PTP1B/D181A/Q262A.

In these methods, the substrate of the PTP can be any substrate, particularly a protein, that binds to, associates with, or interacts with the PTP. For example, the substrate of the PTP may be a tyrosine phosphorylated protein. Examples of tyrosine phosphorylated proteins that may be suitable substrates for a PTP include, without limitation, p130$^{cas}$, the EGF receptor, p210$^{bcr-abl}$, c-Src kinase, the insulin receptor, p160, p120, p70, and p60.

In these methods, a candidate substrate is contacted with at least one substrate-trapping PTP in which the invariant aspartate residue and the invariant glutamine residue are each replaced with a replacement amino acid residue. To effect contact, the candidate substrate may be combined with the substrate-trapping PTP complex between the candidate substrate and the substrate-trapping PTP, thereby producing a combination. For example, contacting may be effected in vitro, under conditions suitable for binding of the candidate substrate to the substrate-trapping PTP enzyme, for a period of time sufficient to permit binding of the candidate substrate to the substrate-trapping PTP. Appropriate binding conditions (e.g., temperature, pH, and salt concentration) are readily determinable by the skilled artisan.

After the candidate substrate has been combined with, or contacted with, the substrate-trapping PTP, an assessment may be made of the ability of the candidate substrate to bind to the PTP. For example, it may be determined whether or not a complex between the candidate substrate and the substrate-trapping PTP is present in the enzyme/substrate combination. In these embodiments, the presence of a complex in the combination between the candidate substrate and the substrate-trapping PTP is indicative that the candidate substrate is a substrate of the PTP.

The present invention is also directed to kits for identifying a substrate of a PTP. The kits comprise the following: (a) at least one of the previously described PTP mutants in which the invariant aspartate residue and the invariant glutamine residue are each replaced with a replacement amino acid residue; and (b) one or more ancillary reagents suitable for use in detecting binding of the PTP enzyme to a candidate substrate. The kits optionally may further comprise a container and/or instructions for utilizing the mutant and the reagent(s) to identify a PTP substrate.

In the kits of the present invention, the PTP may be any member of the PTP family, as previously discussed. Also, the candidate substrate of the PTP may be any substrate, e.g., a protein or oligopeptide, that binds to, associates with, or interacts with the PTP. For example, the substrate of the PTP may be a tyrosine phosphorylated protein. Examples of tyrosine phosphorylated proteins that may be suitable substrates for a PTP include, without limitation, $p130^{cas}$, the EGF receptor, $p210^{bcr-abl}$, c-Src kinase, the insulin receptor, p160, p120, p70, and p60.

In these kits, the ancillary reagent or reagents capable of detecting binding of the PTP to the candidate substrate (e.g., by detecting the presence or absence of an enzyme-substrate complex) are preferably secondary antibodies that bind selectively to one or the other of the enzyme and substrate, and which are further linked, either through a covalent linkage or by a noncovalent linkage, to a reporter molecule, including, without limitation, an enzyme, a fluorescent molecule, a light-emitting molecule, or a radioactive molecule. If the agent if located on a cell surface, antibody binding to the cell may result in cell agglutination. In such a case, the reagent capable of detecting the resulting complex will not be necessary.

The double mutant PTP of the present invention may be useful for reducing the activity of a substrate of a PTP. Accordingly, the present invention further provides a method for reducing in vivo the activity of a substrate of a PTP in a subject, comprising administering to the subject a mutant PTP in which the invariant aspartate residue is replaced with a replacement amino acid residue and the invariant glutamine residue is replaced with a replacement amino acid residue, and which forms a complex with the substrate. The subject is preferably a mammal (e.g., a human; a domestic animal; or a commercial animal, including a cow, a dog, a mouse, a monkey, a pig, and a rat), and is most preferably a human. The double mutant PTP is administered to the subject in an amount effective to reduce the activity of the substrate of the PTP. This amount may be readily determined by the skilled artisan.

The previously described double mutant PTPs of the present invention are suitable for reducing the activity of a substrate of a PTP, particularly a tyrosine phosphorylated protein, because it is capable of binding the phosphorylated protein without dephosphorylating the protein. As such, the double mutant PTP will form a complex with the substrate, thereby reducing its downstream effects.

The double mutant PTP of the present invention may be administered to a human or animal subject by known procedures, including, without limitation, nasal administration, oral administration, parenteral administration (e.g., epidural, epifascial, intracapsular, intracutaneous, intradermal, intramuscular, intraorbital, intraperitoneal [particularly in the case of localized regional therapies], intrasternal, intravascular, intravenous, parenchymatous, and subcutaneous administration), sublingual administration, transdermal administration, and administration by osmotic pump. Preferably, the PTP is administered nasally or orally.

For oral administration, a formulation of the PTP may be presented in solid or liquid preparations, e.g., capsules, tablets, powders, granules, dispersions, solutions, and suspensions. Such preparations are well known in the art, as are other oral-dosage forms not listed here. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulations also may be presented with dibasic calcium phosphate anhydrous or sodium starch glycolate. Finally, the formulation may be presented with lubricants, such as talc or magnesium stearate.

For parenteral administration, a formulation of the PTP may be combined with a sterile aqueous solution that is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampules or vials. The formulation may be delivered by any mode of injection, including, without limitation, epidural, epifascial, intracapsular, intracutaneous, intradermal, intramuscular, intraorbital, intraperitoneal (particularly in the case of localized regional therapies), intrastemal, intravascular, intravenous, parenchymatous, or subcutaneous.

For transdermal administration, a formulation of the PTP may be combined with skin penetration enhancers, such as propylene glycol, polyethylene glycol, isopropanol, ethanol, oleic acid, N-methylpyrrolidone, and the like, which increase the permeability of the skin to the enzyme, and permit the enzyme to penetrate through the skin and into the bloodstream. The composition of the enhancer and the enzyme also may be further combined with a polymeric substance, such as ethylcellulose, hydroxypropyl cellulose, ethylene/vinylacetate, polyvinyl pyrrolidone, and the like, to provide the composition in gel form, which may be dissolved in a solvent, such as methylene chloride, evaporated to the desired viscosity, and then applied to backing material to provide a patch. For nasal administration, aerosol, nasal-mist, or nasal-spray a formulation of the PTP may be prepared in accordance with standard procedures known in the art for the preparation of nasal sprays.

A formulation of the PTP also may be released or delivered from an osmotic mini-pump or other time-release device. The release rate from an elementary osmotic mini-pump may be modulated with a microporous, fast-response gel disposed in the release orifice. An osmotic mini-pump would be useful for controlling release, or targeting delivery, of the enzyme.

In accordance with the methods of the present invention, the PTP may be administered to a subject by introducing to the subject the protein itself, or by introducing to the subject DNA encoding the enzyme, in a manner permitting expression of the protein. The enzyme of the present invention may be introduced to the subject by known techniques used for the introduction of drugs, including, for example, injection and transfusion. For non-invasive introduction of the PTP of the present invention, micro-encapsulated preparations, such as liposomes, also may be used. Liposomal vesicles may be prepared by various methods known in the art, and liposome compositions may be prepared using any one of a variety of conventional techniques for liposome preparation known to those skilled in the art.

DNA encoding the PTP may be introduced to the subject using conventional procedures known in the art, including, without limitation, electroporation, DEAE dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, and naked DNA transfer, or any combination thereof. Recombinant viral vectors suitable for gene therapy include, but are not limited to, vectors derived from the genomes of viruses such as a retrovirus, HSV, adenovirus, adeno-associated virus, Semiliki Forest virus, cytomegalovirus, and vaccinia virus.

The present invention is further directed to methods for identifying an agent that alters interaction between a PTP and a substrate of the PTP. The methods, comprising the steps of: (a) identifying a substrate of a PTP using a method described herein; (b) contacting the PTP and the substrate, in the presence of a candidate agent; and (c) assessing the ability of the candidate agent to inhibit PTP-substrate interaction. Also provided is an agent identified in accordance with this method. An agent identified by the method of the present invention may be an antagonist, such as an agent that inhibits or decreases activity of a PTP. Additionally, an agent identified by the method of the present invention may be an agonist, such as an agent that enhances or increases PTP activity. An agent that is capable of altering interaction between a PTP and a substrate thereof also may be an agent that interacts with the PTP.

As used herein, an "agent" shall include a protein, polypeptide, peptide, nucleic acid (including DNA or RNA), antibody, Fab fragment, F(ab')$_2$ fragment, molecule, compound, antibiotic, drug, and any combinations thereof. Moreover, an agent may be either natural or synthetic, and exogenous or endogenous. A Fab fragment is a univalent antigen-binding fragment of an antibody, which is produced by papain digestion. An F(ab')$_2$ fragment is a divalent antigen-binding fragment of an antibody, which is produced by pepsin digestion. As used herein, the antibody of the present invention may be polyclonal or monoclonal, and may be produced by techniques well known to those skilled in the art. Polyclonal antibody, for example, may be produced by immunizing a mouse, rabbit, or rat with purified protein. Monoclonal antibody may then be produced by removing the spleen from the immunized mouse, and fusing the spleen cells with myeloma cells to form a hybridoma which, when grown in culture, will produce a monoclonal antibody. The antibody of the present invention also includes a humanized antibody, made in accordance with procedures known in the art.

According to the method of the present invention, an agent that alters (inhibits or enhances) interaction between a PTP and a substrate of the PTP may be identified by: identifying a substrate of a PTP using a method described herein; contacting the PTP and the substrate in the presence of a candidate agent; and assessing the ability of the candidate agent to inhibit PTP-substrate interaction. A substrate of a PTP may be identified in accordance with the above-described method for identifying a substrate of a PTP, which comprises the steps of: (a) contacting a candidate substrate with at least one PTP in which the invariant aspartate residue and the invariant glutamine residue are each replaced with a replacement amino acid residue, wherein the replacement residues together cause a reduction in catalytic rate ($k_{cat}$) of the enzyme and an increase in substrate-binding affinity ($K_d$) of the enzyme; and (b) assessing the ability of the candidate agent to bind to the PTP.

In accordance with the method of the present invention, a PTP may be contacted with a substrate that has been identified in the manner described above, in the presence of a candidate agent. To effect contact, the substrate may be combined with the substrate-trapping PTP, in the presence of a candidate agent, under conditions appropriate for binding or formation of a complex between the substrate and the substrate-trapping PTP, thereby producing a combination. For example, contacting may be effected in vitro, under conditions suitable for binding of the substrate to the substrate-trapping PTP enzyme, for a period of time sufficient to permit binding of the substrate to the substrate-trapping PTP enzyme. Appropriate binding conditions (e.g., temperature, pH, and salt concentration) may be readily determinable by the skilled artisan.

After the substrate has been combined with, or contacted with, the substrate-trapping PTP, in the presence of the candidate agent, an assessment may be made of the ability of the candidate agent to alter (inhibit or enhance) interaction or binding between the PTP and the substrate. For example, the amount of enzymatic activity (or extent of binding) in the combination may be determined in the presence of the candidate agent, under conditions suitable for the formation of an enzyme-substrate complex, and this may be compared with the amount of enzymatic activity (or extent of binding) in the combination in the absence of the candidate agent under conditions suitable for the formation of an enzyme-substrate complex. In this embodiment of the present invention, a difference in enzymatic activity (or extent of binding) in the combination in the presence of the candidate agent, as compared with enzymatic activity (or extent of binding) in the absence of the candidate agent, is indicative that the candidate agent alters (inhibits or enhances) interaction between a PTP and a substrate of the PTP or interacts with a PTP.

An agent that alters (inhibits or enhances) interaction between a PTP and a substrate of the PTP, or an agent that interacts with a PTP, may be identified using an in vitro assay, such as an ELISA. Moreover, a specific inhibitor of PTP enzyme/substrate interaction may be obtained by high-throughput screening of a small-molecule library using purified PTP. Additionally, an agent that alters interaction between a PTP and a substrate of the PTP, or an agent that interacts with a PTP, may be identified using an in vivo assay, such as a yeast two-hybrid system.

The present invention is described in the following Experimental Details section, which is set forth to aid in the understanding of the invention, and should not be construed to limit in any way the scope of the invention as defined in the claims which follow thereafter.

EXPERIMENTAL DETAILS

1. Introduction

As described above, detailed mechanistic studies have shown that members of the protein tyrosine phosphatase (PTP) family utilize a common mechanism for phosphomonoester hydrolysis (FIG. 1) (5). Although PTPs share a common mechanism of action (hydrolysis of phosphotyrosine), the cellular processes in which they are involved can be both highly specialized and fundamentally important. It is believed that identification of cellular PTP substrates will help elucidate the biological functions of individual PTPs.

To date, two types of substrate-trapping mutants have been used to isolate PTP substrates. In the first, the active site Cys residue is replaced by a Ser (e.g., PTP1B/C215S); in the second, the general acid Asp residue is substituted by an Ala (e.g., PTP1B/D181A). Unfortunately, only a limited number of substrates (usually cellular proteins that are relatively abundant) have been identified with these two mutants.

Based upon mechanistic considerations, the inventors created novel PTP double mutants with improved substrate-trapping properties. These double mutants are described herein. Kinetic and thermodynamic characterization of the newly-designed PTP1B mutants indicate that PTP1B/D181A/Q262A displays lower catalytic activity than does D181A. In addition, PTP1B/D181A/Q262A possesses substrate-binding affinity that is 6- or 28-fold higher than that of PTP1B/D181A or PTP1B/C215S, respectively. Moreover, in vivo substrate-trapping experiments indicate that the double mutant PTP1B/D181A/Q262A exhibits much higher affinity for a bona fide PTP1B substrate, the epidermal growth factor receptor (EGFR), than does either PTP1B/D181A or PTP1B/C215S. Finally, the double mutant PTP1B/D181A/Q262A also trapped several novel, less abundant PTP1B substrates that are missed by both D181A and C215S mutants.

Accordingly, the inventors' newly-developed and improved substrate-trapping double mutant can serve as a powerful affinity reagent to isolate and purify both high- and low-abundance protein substrates. Given that both Asp181 and Gln262 are invariant among the PTP family, it is expected that this improved substrate-trapping mutant would be appropriate for identifying substrates for all members of the PTP family.

2. Materials and Methods

A. Materials p-nitrophenyl phosphate (pNPP) was purchased from Fluka Co. Other chemicals were purchased from Fisher Co. Solutions were prepared using deionized and distilled water. The preparation of the nonhydrolyzable phosphotyrosine (pTyr) mimetic phosphonodifluoromethyl phenylalanine- ($F_2$Pmp-) containing peptide, Ac-Asp-Ala-Asp-Glu-$F_2$Pmp-Leu-$NH_2$, was previously described (24). Recombinant human epidermal growth factor (EGF) was purchased from Upstate Biotechnology (Lake Placid, N.Y.). Anti-hemagglutinin (anti-HA) epitope mouse monoclonal antibody IgG-horseradish peroxidase (HRP) conjugate, anti-phosphotyrosine antibody PY20 and PY99 horseradish peroxidase conjugated, anti-HA conjugated agarose for immunoprecipitation, rabbit anti-EGF receptor polyclonal antibody, and goat anti-rabbit IgG-HRP were all purchased from Santa Cruz Biotechnology.

B. Protein Expression and Purification

The catalytic domain of PTP1B (residues 1 to 321) was used for in vitro study. PTP1B mutants, C215S, D181A, and Q262A, were described previously (9, 25, 26). PTP1B double mutants, D181A/C215S and C215S/Q262A, were generated by PCR reactions, according to the standard procedure of the Quick-Change™ site-directed mutagenesis kit (Stratagene), using pT7-7/PTP1B/C215S as a template. PTP1B double mutants, D181A/C215E and D181A/Q262A, were generated by similar PCR procedures, using pT7-7/PTP1B/D181A as a template. The recombinant wild-type and mutant PTP1Bs were expressed in E. coli, and purified to homogeneity as described (25, 27). Protein concentration was determined from absorbance measurement at 280 nm, using an absorbance coefficient of 1.24 for 1 mg/ml PTP1B.

C. Determination of Kinetic Constants Using pNPP as a Substrate

PTP activity was assayed at 25° C. and pH 7.0, in a reaction mixture (0.2 ml) containing pNPP concentrations ranging from 0.2 to 5 $K_m$. The following buffered solution was used for activity measurements: pH 7.0, 50 mM 3,3-dimethylglutarate, 1 mM EDTA; the ionic strength was 0.15 M, as adjusted by addition of NaCl. Initial rate measurements for the enzyme-catalyzed hydrolysis of pNPP were conducted as previously described (26). Michaelis-Menten kinetic parameters were determined from a direct fit of the data to the Michaelis-Menten equation, using the nonlinear regression program, KINETASYST (Intellikinetics, State College, Pa.).

D. Determination of Kinetic Constants Using pTyr-containing Peptides as Substrates All assays were performed at 25° C. in buffer (pH 7.0, ionic strength=0.15 M) containing 50 mM 3,3-dimethylglutarate and 1 mM EDTA. A continuous spectrophotometric assay, previously described (28), was employed to determine $k_{cat}$ and $K_m$ for the pTyr-containing peptides. The dephosphorylation reaction was monitored by either an increase in absorbance at 282 nm, or an increase in fluorescence at 305 nm. Fluorometric and absorbance determinations were performed on a Perkin-Elmer LS50B fluorometer and a Perkin-Elmer Lambda 14 spectrophotometer, respectively. The instruments were equipped with a water-jacketed cell holder, permitting maintenance of the reaction mixture at the desired temperature (25° C.).

E. Isothermal Titration Calorimetry

All isothermal titration calorimetry experiments were performed using an MCS Isothermal Titration Calorimetry System from Microcal Inc. (Northampton, Mass.). Experiments at pH 7.0 were conducted at 25° C., in 50 mM 3,3-dimethylglutarate buffer containing 1 mM DTT. The ionic strength of the buffer was adjusted to 0.15 M by addition of NaCl. Protein concentration in the calorimeter cell was 27-85 µM, while the ligand concentration in the syringe was 0.37-1 mM.

The PTP1B samples used in the isothermal titration calorimetry experiments were dialyzed completely against buffer. High-concentration stock solutions were prepared for ligands with distilled water, and adjusted to pH 7.0. Stock was diluted at least 26-fold with 50 mM 3,3-dimethylglutarate buffer before titration. Protein dilution during titration was determined by titration of buffer into the protein solution. The heat of protein dilution was found to be negligible. The heat of ligand dilution was corrected by subtracting the average heat of injection after saturation.

The binding data were analyzed using ORIGIN software (29). Binding constant, K, and enthalpy change, ΔH, were used to calculate free energy change, ΔG, and entropy change, ΔS, according to equation [1]:

$$-RTLnK = \Delta G = \Delta H - T\Delta S \qquad [1]$$

where R is the gas constant and T is the absolute temperature.

F. Mammalian Expression Plasmids

The hemagglutinin-tagged (HA-tagged) full-length human wild-type PTP1B in pJ3H expression vector was a gift from Dr. Chernoff (30). The HA-tagged PTP1B mutants, C215S, D181A, D181A/C215S, and D181A/Q262A, were generated by PCR reactions, according to the standard procedure of the Quick-Change™ site-directed mutagenesis kit (Stratagene), using pJ3H-HA-PTP1B as a template. All mutations were verified by DNA sequencing.

G. Cell Culture and Transient Transfection

Monkey kidney COS1 cells (ATCC: CRL-1650) were maintained in Dulbecco's modified Eagle's minimum essential medium (DMEM), supplemented with 10% fetal bovine serum (Life Technologies, Inc.), penicillin (50 units/ml), streptomycin (50 µg/ml), and L-glutamine (2 mM) under a humidified atmosphere containing 5% $CO_2$. In transient transfection experiments, COS1 cells were inoculated at a density of $2 \times 10^5$ cells/60-mm dish, and grown overnight in DMEM containing 10% fetal bovine serum. Transfection was performed using LipoTAXI$^R$ according to the manufacturer's recommendations (Stratagene, Cedar Creek, Tex.). Each transfection assay included 4 µg of purified DNA mixed with LipoTAXI[R] in a 1:5 DNA:lipid ratio per 60-mm dish of cells. Following transfection, the cells were exchanged to normal culture medium, and maintained for 44 to 48 h at 37° C. and 5% $CO_2$. The efficiency of transfection, as assessed by 5-bromo-4-chloro-3-indolyl-β-D galactoside (X-Gal) staining of pCMV-β-gal-transfected (β-Gal staining kit, Invitrogen) COS cells, was 25%.

H. Cell Lysis, Immunoprecipitation, and Western Blotting

The transfected cells (treated with or without EGF) were lysed with "lysis buffer" containing 50 mM Tris-HCl (pH 7.5), 5 mM EDTA, 150 mM NaCl, 10 mM sodium phosphate, 10 mM sodium fluoride, 5 mM iodoacetic acid, 1 mM benzamidine, 1% Triton X-100, 10 µg/ml leupeptin, and 5 µg/ml Aprotinin. Lysate protein concentration was estimated using Bio-Rad protein assay reagent (Bio-Rad, Hercules, Calif.).

For immunoprecipitation, 1 mg of cell lysate was immunoprecipitated overnight with 30 µl of agarose-conjugated anti-hemagglutinin antibody at 4° C. Immunocomplexes were washed four times with the cell lysis buffer, and boiled for 5 min in SDS-PAGE sample buffer. Proteins in the cell lysate were separated by 8% SDS-PAGE under reducing conditions, according to the method of Laemmli (31), followed by blotting onto nitrocellulose membranes (Protran, Schleicher & Schuell). The nitrocellulose membranes were blocked with 5% non-fat dry milk in Tris-buffered saline/Tween (TBST) buffer (20 mM Tris-HCl, 150 mM NaCl, 0.1% Tween-20; pH 7.6) for 1 h at 25° C.

Thereafter, blots were incubated overnight with primary antibodies diluted in TBST containing 5% non-fat dry milk at 4° C. The blots were then rinsed with TBST (3 times), for 5 min at 25° C., and incubated with the appropriate secondary antibody diluted in TBST containing 5% non-fat dry milk, for 1 h at 25° C. The blots were rinsed 3 more times with TBST for 5 min before detection by enhanced chemiluminescence (ECL) (Cell Signaling Technology). For re-probing, blots were stripped by incubating in 62.5 mM Tris-HCl, 2% SDS, and 100 mM 2-mercaptoethanol (pH 6.7) for 30 min at 50° C. Stripped blots were then rinsed extensively with TBST, and re-probed as described above.

3. Results and Discussion

PTPs play a central role in controlling many diverse signal transduction pathways in cells. Although PTPs share a common catalytic mechanism (hydrolysis of phosphoamino acids), they have distinct (and often unique) biological functions in vivo. Genetics and biochemical studies indicate that PTPs are involved in a number of disease processes (3). However, despite the detailed understanding of PTP catalysis, the molecular basis for the diverse biological functions of PTPs is poorly understood. In part, this lack of understanding is a result of the paucity of information concerning the physiological substrates of most PTPs. Therefore, the identification of physiological substrates for individual PTPs remains one of the central goals in this field. One effective strategy for identifying and characterizing in vivo PTP substrates employs high affinity PTP substrate-trapping mutants.

Currently, two types of substrate-trapping mutants are being used to identify PTP substrates. In the first mutant, the active site Cys residue is replaced by a Ser, which leads to a complete loss of phosphatase activity (14-16, 32). In the second, the general acid Asp residue is substituted by an Ala (17, 18), which results in a decrease in $k_{cat}$ of several orders of magnitude (8, 18). So far, only relatively abundant cellular proteins have been identified with these two mutants. It is possible that the affinity for substrates of the existing trapping mutants is not high enough to enable the capture of less abundant proteins.

The goal of the present study is to create a mutant PTP with enhanced substrate-trapping properties, for use in PTP substrate identification. The inventors' strategy to achieve this goal is to exploit the common mechanism of PTP catalysis to create substrate-trapping mutants that can be applied to all PTP members. In doing so, the inventors decided to focus on invariant residues that are important for PTP catalysis.

There are two ways to improve a substrate-trapping mutant: (1) by lowering the dissociation constant ($K_d$) between the enzyme and the substrate; and (2) by further slowing down substrate turnover ($k_{cat}$). Since PTP1B/D181A displays higher affinity for substrates than does PTP1B/C215S, both in vitro and in vivo (18, 24), the inventors sought to improve its potency by introducing into it a second site mutation. Because the general acid deficient mutant PTP1B/D181A still contains residual phosphatase activity, the inventors considered mutating additional invariant residues to further reduce its activity, and possibly to further increase its substrate-binding affinity. The criteria for selecting the second site mutations are as follows: (1) mutation of the second residue must lead either to a further decrease in activity or to an increase in affinity; and (2) mutation of the second residue must not alter substrate specificity. Thus, the chosen residues ideally should be located in or near the active-site pocket (i.e., pTyr binding site), and should perform universal catalytic functions.

In view of the above criteria, the active site Cys215 is an obvious choice because of its essential role in catalysis. Thus, substitutions of Cys215 in PTP1B/D181A should render the double mutant inactive. However, because the side chain of the active site Cys exists as a thiolate anion at physiological pH (33), the Cys-to-Ser mutation is not a simple substitution of OH for SH; rather, it is a replacement of the negatively charged thiolate anion with a neutral hydroxyl group. Indeed, the inventors have observed that the Cys-to-Ser mutation causes significant structural/dynamic perturbations in the active site (24, 32, 34, 35). Therefore, in addition to PTP1B/D181A/C215S, the inventors also prepared PTP1B/D181A/C215E in order to mimic the thiolate anion in the active site.

The next residue that the inventors chose was Gln262, which is invariant among all PTPs (FIG. 2). The crystal structure of PTP1B/C215S bound with Ac-DADEpYL-NH$_2$ showed that the side chain of Gln262 is close to the phenyl ring of pTyr, and may define a portion of the rim for the pTyr binding pocket (37). Previous kinetic studies revealed that the $k_{cat}/K_m$ and $k_{cat}$ for the PTP1B/Q262A-catalyzed hydrolysis of the epidermal growth factor receptor peptide, DADEpYLIPQQG (SEQ ID NO:2)(EGFR[988-998]), and phosphorylated lysozyme were reduced by 10- and 100-fold, respectively (18, 26). This suggests that Gln262 may play a role in both the formation of the thiophosphoryl enzyme intermediate (E-P) and the E-P hydrolysis step. Studies on the structural equivalents, Gln446 in the *Yersinia* PTP (36) and Gln262 in PTP1B (38), also suggest that the invariant Gln262 residue is important for the optimal positioning of the nucleophilic water molecule, which facilitates efficient E-P hydrolysis (FIG. 1). To determine whether mutation of Gln262 would improve existing substrate-trapping mutants, the inventors prepared PTP1B/C215S/Q262A and PTP1B/D181A/D262A.

A. Kinetic Characterization

All recombinant PTP1B proteins were expressed in *Escherichia coli*, and purified to near homogeneity, as judged by SDS polyacrylamide gel electrophoresis, using procedures described previously (25, 27) (data not shown). The kinetic parameters for the wild-type and mutant PTP1B-catalyzed hydrolysis of pNPP are summarized in Table 1.

TABLE 1

Kinetic Parameters for the Wild-type and Mutant
PTP1B-Catalyzed Hydrolysis of pNPP

| PTP1B | $K_m$(μM) | $k_{cat}$(s$^{-1}$) | $k_{cat}/K_m$(M$^{-1}$ s$^{-1}$) |
|---|---|---|---|
| [a]Wild-type | 2400 ± 200 | 9.8 ± 0.5 | (4.1 ± 0.4) × 10$^3$ |
| [a]D181A | 80 ± 30 | (3.1 ± 0.3) × 10$^{-2}$ | (3.9 ± 1.5) × 10$^2$ |
| [b]Q262A | 58 ± 6 | 0.21 ± 0.01 | (3.6 ± 0.3) × 10$^3$ |
| [a]D181A/Q262A | 2.4 ± 0.5 | (2.8 ± 0.1) × 10$^{-3}$ | (1.2 ± 0.2) × 10$^3$ |
| [c]C215S | | | |
| [c]D181A/C215S | | | |
| [c]C215S/Q262A | | | |
| [c]D181A/C215E | | | |

[a]Measured at 25° C. and pH 7.0.
[b]Measured at 30° C. and pH 7.0 (26).
[c]No measurable activities were observed for C215S, C215S/D181A, C215S/Q262A, and D181A/C215E.

Table 2 lists the steady-state kinetic parameters for the wild-type and mutant PTP1Bs, using the EGFR$^{988-998}$ peptide DADEpYLIPQQG as a substrate. As expected, no measurable activities were observed for C215S, D181A/C215S, C215S/Q262A, and D181A/C215E. For the D181A mutant, the $k_{cat}$ was 320-fold lower than that of the wild-type enzyme, while the $K_m$ value was 30-fold lower with pNPP as a substrate (Table 1). With the EGFR$^{988-998}$ peptide as a substrate, the $k_{cat}$ value for D181A was 920-fold lower than that for PTP1B, while the $K_m$ value was 22-fold higher (Table 2). As shown previously, Q262A exhibited 38- and 7.4-fold decreases in $K_m$ for pNPP and the EGFR$^{988-998}$ peptide, respectively (26). In addition, the $k_{cat}$ for the Q262A-catalyzed hydrolysis of pNPP and the EGFR$^{988-998}$ peptide was reduced by 80- and 150-fold, respectively (26).

TABLE 2

Kinetic Parameters for the Wild-type and Mutant PTP1B-Catalyzed
Hydrolysis of the EGFR$^{988-998}$ peptide, DADEpYLIPQQG

| PTP1B | $K_m$(μM) | $k_{cat}$(s$^-$) | $k_{cat}/K_m$(M$^{-1}$ s$^{-1}$) |
|---|---|---|---|
| [a]Wild-type | 2.6 ± 0.3 | 30 ± 1 | (1.2 ± 0.1) × 10$^7$ |
| [1]D181A | 56 ± 2 | (6.5 ± 0.2) × 10$^{-2}$ | (1.2 ± 0.1) × 10$^3$ |
| [b]Q262A | 0.35 ± 0.05 | 0.29 ± 0.002 | (8.3 ± 1.1) × 10$^5$ |
| [a]D181A/Q262A | 51 ± 4 | (2.7 ± 0.1) × 10$^{-3}$ | (5.3 ± 0.5) × 10$^1$ |

[a]Measured at 25° C. and pH 7.0.
[b]Measured at 30° C. and pH 7.0 (26).

The substitution of Gln262 by an Ala in D181A resulted in a 33-fold decrease in $K_m$, and an 11-fold decrease in $k_{cat}$, with pNPP as a substrate (Table 1). Interestingly, with the EGFR$^{988-998}$ peptide as a substrate, the $k_{cat}$ for D181A/Q262A was 24-fold lower than that for D181A, while the $K_m$ value for D181A/Q262A was similar to that for D181A (Table 2). Collectively, then, it appears that mutation at either Asp181 or Gln262 results in large reductions in $k_{cat}$, irrespective of the substrates, and that the $k_{cat}$ for the double mutant is lower than those for the single mutants.

B. The Kinetic Parameter $K_m$ Is Not an Accurate Indicator of Substrate-Binding Affinity The overall mechanism of the PTP-catalyzed reaction involves a number of steps that are represented schematically in Scheme 1, where ArOPO$_3^{2-}$ can be either aryl phosphates or pTyr-containing peptides/proteins. The reaction proceeds through a sequence involving substrate binding (substrate dissociation constant $K_s$=$k_{-1}$/$k_1$), which is then cleaved with phosphoryl transfer ($k_2$) to the active site nucleophilic Cys residue (E-P formation). A subsequent general base-catalyzed reaction with water cleaves the phosphoenzyme intermediate E-P ($k_3$), and the release of phosphate completes the catalytic cycle.

Applying the steady-state assumption to [E-P], it can be shown that $k_{cat}$=[$k_2k_3/(k_2+k_3)$] and $K_m$=[$K_sk_3/(k_2+k_3)$]. Thus, the $k_{cat}$ term describes the rate-limiting step under saturating concentrations of substrate, and is mostly determined by the E-P hydrolysis step ($k_3$) for the wild-type PTP1B (26, 39). The $K_m$ parameter is an apparent dissociation constant that can be treated as the overall dissociation constant of all enzyme-bound species (40). For example, when $k_2$ is much greater than $k_3$, the concentration of E-P is much greater than [E•ArOPO$_3^{2-}$], so that E-P contributes more to $K_m$ than does E•ArOPO$_3^{2-}$, and is the predominant enzyme-bound species. Thus, $K_m$ is not an accurate measure of substrate-binding affinity. Rather, its value is smaller than the substrate-dissociation constant $K_s$ by a factor of $k_3/(k_2+k_3)$.

Scheme 1

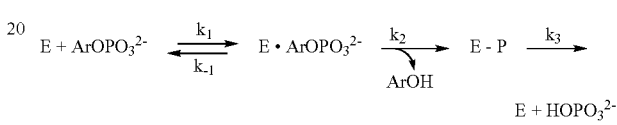

The dramatic decrease in $K_m$ for the Q262A mutant, which may be indicative of increased accumulation of the E-P intermediate in the Q262A-catalyzed reactions, is consistent with the observation that substitution of Gln262 by an Ala has a more severe effect on $k_3$ than on $k_2$ (26, 37). Interestingly, it appears that, for both D181A and the double mutant D181A/Q262A, the mutation may have a more negative effect on $k_3$ in the pNPP reaction, resulting in a decrease in $K_m$. In contrast, in the peptide-substrate reaction, the mutation may have a more deleterious effect on $k_2$, leading to an increase in $K_m$. Thus, it is difficult to predict the substrate-binding affinity of the double mutant (D181A/Q262A) based purely upon the apparent $K_m$ values.

C. D181A/Q262A Displays Higher Affinity to Ac-Asp-Ala-Asp-Glu-F$_2$Pmp-Leu-NH$_2$ than Does D181A To determine directly the substrate-binding affinity for substrates of the PTP1B double mutants, the inventors performed isothermal titration microcalorimetry (ITC) experiments. ITC allows a simultaneous determination of the binding constant (K), stoichiometry, and the enthalpy change (ΔH) associated with the binding of a ligand to a macromolecule (29). From these parameters, the Gibbs free energy of binding (ΔG) and the entropy change (ΔS) of binding can also be derived from the expression ΔG=−RTLnK=ΔH-TΔS. Because of the inherent hydrolytic activity, it has not been possible to study directly the binding interactions between a PTP and its substrate. In order to compare binding interactions between wild-type PTP1B and its various mutants (either active or inactive), the inventors have used peptides that contain a nonhydrolyzable pTyr analog, phosphonodifluoromethyl phenylalanine (F$_2$Pmp), in the ITC experiments (24).

The F$_2$Pmp-containing peptide, Ac-Asp-Ala-Asp-Glu-F$_2$Pmp-Leu-NH$_2$, is an excellent non-hydrolyzable substrate analog that exhibits high affinity for PTP1B (24, 41, 42). Using ITC, the inventors have previously determined the dissociation constant ($K_d$) and thermodynamic parameters for the binding of Ac-Asp-Ala-Asp-Glu-F$_2$Pmp-Leu-NH$_2$ to PTP1B and to the mutants, C215S and D181A (24). The inventors showed that the active site Cys215-to-Ser mutant PTP1B binds Ac-Asp-Ala-Asp-Glu-F$_2$Pmp-Leu-NH$_2$ with the same affinity as the wild-type enzyme (Table 3). In addition, the inventors found that the general acid deficient mutant D181A binds the same ligand 5-fold tighter than the C215S mutant, consistent with the observation that the Asp to Ala mutant is a better substrate-trapping reagent than C215S (17, 18).

TABLE 3

Thermodynamic Parameters for the Binding of PTP1B and Its Substrate-Trapping Mutants with Ac-Asp-Ala-Asp-Glu-F$_2$Pmp-Leu-NH$_2$

| PTP1B | $K_d$ (μM) | ΔH (kcal mol$^{-1}$) | TΔS (kcal mol$^{-1}$) | ΔG (kcal mol$^{-1}$) |
|---|---|---|---|---|
| [a]Wild-type | 0.24 ± 0.05 | −3.9 ± 0.2 | 5.1 ± 0.2 | −9.0 ± 0.1 |
| [a]C215S | 0.19 ± 0.03 | −10.4 ± 0.2 | −1.2 ± 0.2 | −9.2 ± 0.1 |
| [a]D181A | 0.04 ± 0.01 | −6.5 ± 0.1 | 3.7 ± 0.1 | −10.2 ± 0.1 |
| [b]D181A/Q262A | 0.0068 ± 0.0023 | −4.5 ± 0.5 | 6.6 ± 0.2 | −11.1 ± 0.2 |
| [b]D181A/C215E | 1.3 ± 0.09 | −28.4 ± 0.3 | −20.4 ± 0.3 | −8.0 ± 0.03 |

All experiments were performed at 25° C. and pH 7.0.
[a]Data from (24).
[b]Data from this study.

Figure 3:
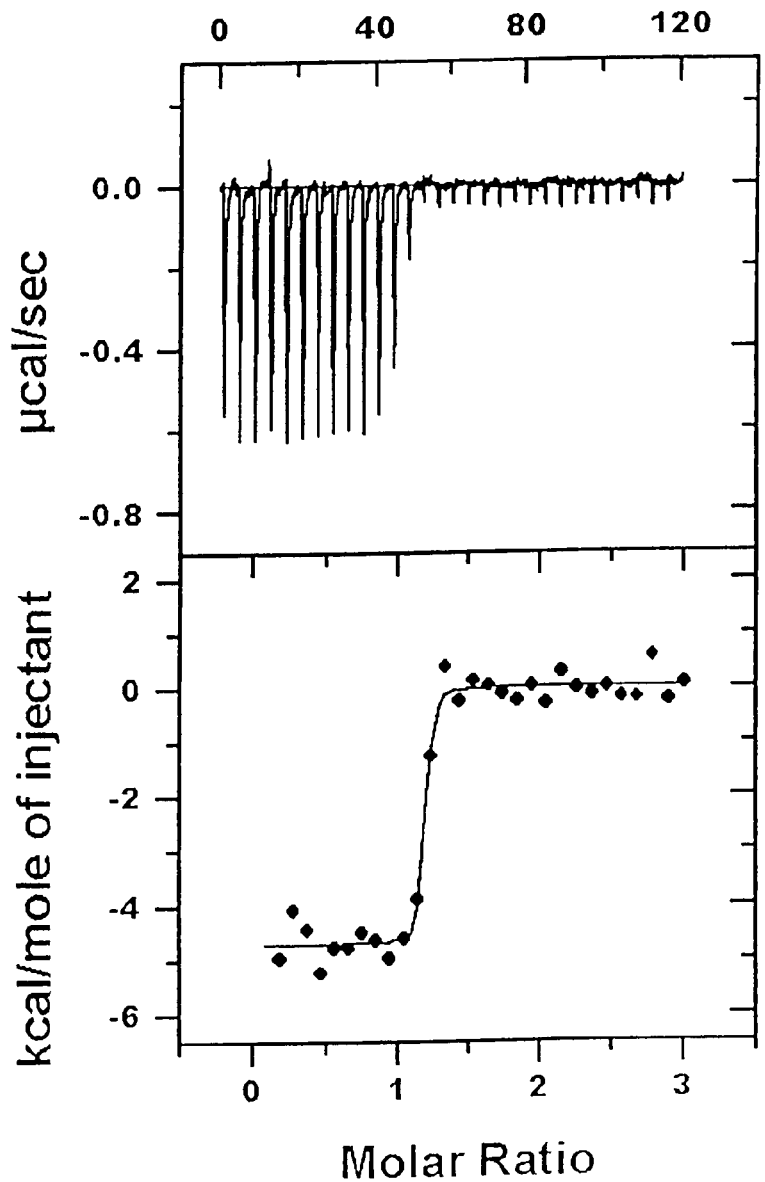
FIG. 3 portrays calorimetric isothermal titration for the reaction of peptide Ac-Asp-Ala-Asp-Glu-F$_2$Pmp-Leu-NH$_2$ with PTP1B/D181A/Q262A. The upper graph depicts raw data for thirty 8-μl injections of the peptide (0.5 mM stock) into the isothermal cell containing 32 μM PTP1B/D181A/Q262A, at 4-min intervals and 25° C. Both the protein and the peptide were in 50 mM 3,3-dimethylglutarate buffer (I=0.15 M, pH 7.0) containing 1 mM DTT. The lower graph depicts an integration curve showing experimental points that were obtained by integration of the above peaks as plotted against the molar ratio of the peptide to PTP1B/D181A/Q262A within the reaction cell. The solid line corresponds to the best fit to the data according to the nonlinear, least-squares regression algorithm, ORIGIN (29).

To determine whether any one of the double mutants (D181A/Q262A, D181A/C215S, D181A/C215E, and C215S/Q262A) displayed improved binding properties over the D181A mutant, the inventors measured the $K_d$ values of the double mutants for Ac-Asp-Ala-Asp-Glu-F$_2$Pmp-Leu-NH$_2$, and the thermodynamic parameters associated with binding, using ITC under conditions (pH 7.0, ionic strength of 0.15 M, and 25° C.) identical to those employed for the wild-type PTP1B and for the C215S and D181A mutants (Table 3). A typical titration curve and binding isotherm for the binding of D181A/Q262A to Ac-Asp-Ala-Asp-Glu-F$_2$Pmp-Leu-NH$_2$ is shown in FIG. 3. From curve-fitting of the binding isotherms, the stoichiometry for the binding of the peptide to D181A/Q262A was determined to be 1:1. The dissociation constant, $K_d$, was 6.8 nM, which is ~30-fold lower than those of the wild-type PTP1B and the C215S mutant (Table 3). More importantly, D181A/Q262A also exhibited nearly 6-fold higher affinity for Ac-Asp-Ala-Asp-Glu-F$_2$Pmp-Leu-NH$_2$ than did the D181A mutant.

The association process between D181A/Q262A and the F$_2$Pmp-containing peptide is both enthalpically (ΔH=−4.5 kcal/mol) and entropically (TΔS=6.6 kcal/mol) favored, yielding a ΔG for binding of −11.1 kcal/mol at pH 7.0 and 25° C. The increased substrate-binding affinity for the D181A/Q262A mutant, as compared with that for the D181A mutant, appears to result from a larger increase in the TΔS term, which more than offsets the smaller decrease in ΔH of binding (Table 3).

The inventors were not able to obtain $K_d$ values for the D181A/C215S and C215S/Q262A mutants because the titration curves were rather complex. The observed titration curves either yielded a very low binding stoichiometry (~0.1 for D181A/C215S), or displayed two peaks (C215S/Q262A) with one absorbing heat and the other releasing heat (data not shown). The inventors noted that, even for the C215S single mutant, the titration curve also displayed two peaks at a lower temperature (15° C.).

Because all of the mutants were purified to homogeneity (i.e., a single band in SDS-PAGE), these observations suggest that the C215S-containing mutants may exist in aqueous solution as an equilibrium mixture of more than one conformation. Indeed, the recently solved crystal structure of the apo PTP1B/C215S mutant showed that C215S can exist in a conformation that is different from that observed in the C215S/substrate complex (43). It is possible that removal of the negative charge from the thiolate group in Cys215 may lead to a disruption of the active-site conformation (24). However, the inventors were able to obtain the $K_d$ and thermodynamic parameters for the binding of Ac-Asp-Ala-Asp-Glu-F$_2$Pmp-Leu-NH$_2$ to D181A/C215E (Table 3). The affinity of D181A/C215E for the peptide ($K_d$=1.3 μM) was 7- and 32-fold lower than those of the C215S and D181A mutants, respectively. Thus, substitution of Cys215 in PTP1B/D181A does not improve PTP1B's affinity for substrates. In contrast, substitution of Gln262 by an Ala in PTP1B/D181A generates a much-improved PTP1B substrate-trapping mutant, with a substrate-binding affinity 6-fold higher than that of PTP1B/D181A.

D. D181A/Q262A Is a Better Substrate-Trapping Mutant than D181A In Vivo

From the experiments described above, the inventors have shown that the D181A/Q262A mutant not only displays lower catalytic activity than the D181A mutant, but also exhibits higher substrate-binding affinity toward a peptide substrate analog. In the following, the inventors present evidence that D181A/Q262A is also a better substrate-trapping mutant in vivo.

To determine whether the double mutant D181A/Q262A also possesses higher affinity for physiological substrates of PTP1B, the inventors performed substrate-trapping experiments in COS1 cells. It has been shown previously that, in COS1 cells, the epidermal growth factor (EGF) receptor is the major substrate for PTP1B, and that the D181A mutant has a higher affinity for the EGF receptor than does the C215S mutant (18). Because EGF receptor is the major PTP1B substrate in COS1 cells, the inventors wanted to determine the effects of expression of PTP1B and its various forms of trapping mutants, in this cell type, on the level of EGF receptor tyrosine phosphorylation.

Figure 4:
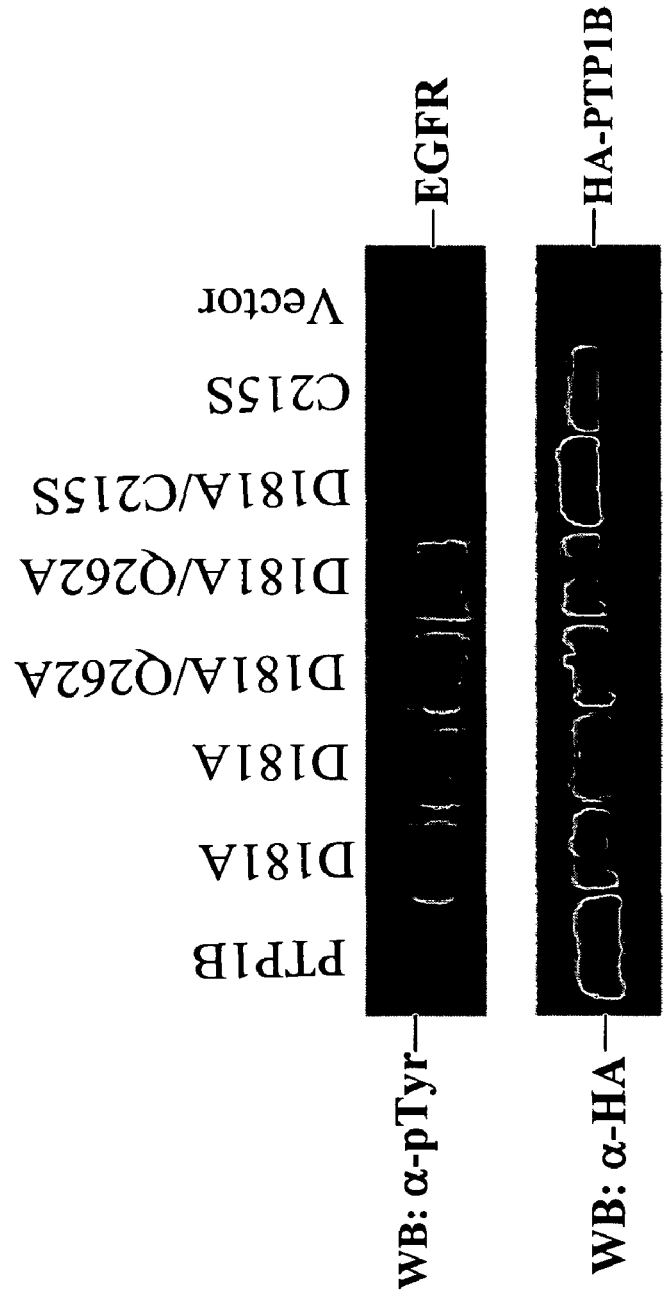
FIG. 4 sets forth Western blots (WB) that show the level of tyrosine phosphorylation in the epidermal growth factor receptor (EGFR) upon expression of the wild-type and mutant PTP1Bs (4 μg plasmid/60 mm dish) in COS1 cells. Samples (50 μg total protein) were taken from the lysates of COS1 cells transfected with 4 μg of pJ3H plasmids expressing HA-tagged wild-type PTP1B, D181A, C215S, D181A/Q262A, or D181A/C215S. These samples were loaded into each lane for SDS-PAGE electrophoresis, and transferred onto a nitrocellulose membrane. The proteins on the membrane were first immunoblotted with anti-pTyr HRP conjugate (upper panel). The membrane was then stripped and re-probed with anti-hemagglutinin (anti-HA) HRP conjugate (lower panel).

Accordingly, the inventors expressed the full-length, HA-tagged wild-type, D181A, C215S, D181A/Q262A, and D181A/C215S mutants of PTP1B in COS1 cells, and then immunoblotted the cell lysates with an anti-pTyr antibody (FIG. 4). The protein expression level of wild-type and mutant PTP1Bs was shown to be similar by Western blotting of the cell lysates using anti-HA antibodies (FIG. 4).

Consistent with earlier work (18), the inventors found that the level of pTyr in the EGF receptor in cells expressing wild-type PTP1B was comparable to that in the vector control. In addition, the inventors also noted that the tyrosine phosphorylation level of EGF receptor was higher in cells expressing the D181A, rather than the C215S, mutant (FIG. 4). These results serve as important controls to demonstrate that, as shown previously, D181A has higher affinity for the EGF receptor than does C215S, and that the trapping mutants bind to and protect substrates from dephosphorylation by endogenous PTPs.

The inventors next evaluated the ability of D181A/Q262A and D181A/C215S to promote accumulation of the pTyr-phosphorylated EGF receptors in COS1 cells. The inventors discovered that D181A/C215S displayed a comparable affinity to that of C215S (FIG. 4). In contrast, the inventors were satisfied to find that enhancement of EGF receptor phosphorylation was most pronounced in cells expressing D181A/Q262A, rather than any other, PTP1B mutants (FIG. 4).

Immunoblotting of the cell lysates with anti-pTyr antibodies showed that, indeed, the D181A/Q262A mutant was much better (more than 3-fold) than the D181A mutant in protecting the phosphorylated EGF receptors in COS1 cells (FIG. 4). These data suggest that D181A/Q262A displays the highest substrate-binding affinity among all mutant forms of PTP1B applied in the inventors' experiments, and that it can strongly protect the EGF receptor from dephosphorylation by the endogenous PTPs.

Finally, the inventors determined whether the binding interaction between the trapping mutants and the substrate would be stable enough to endure isolation procedures. The inventors expressed the wild-type and the mutant forms of PTP1B in COS1 cells. After the cells were treated with EGF (20 ng/ml for 20 min), the expressed PTP1B proteins were immunoprecipitated from the cell lysates using anti-HA antibody-conjugated agarose. The associated substrates were visualized by anti-pTyr and anti-EGFR immunoblotting, and the amount of co-immunoprecipitated PTP1B was measured with HRP-conjugated anti-HA antibody.

Figure 5:
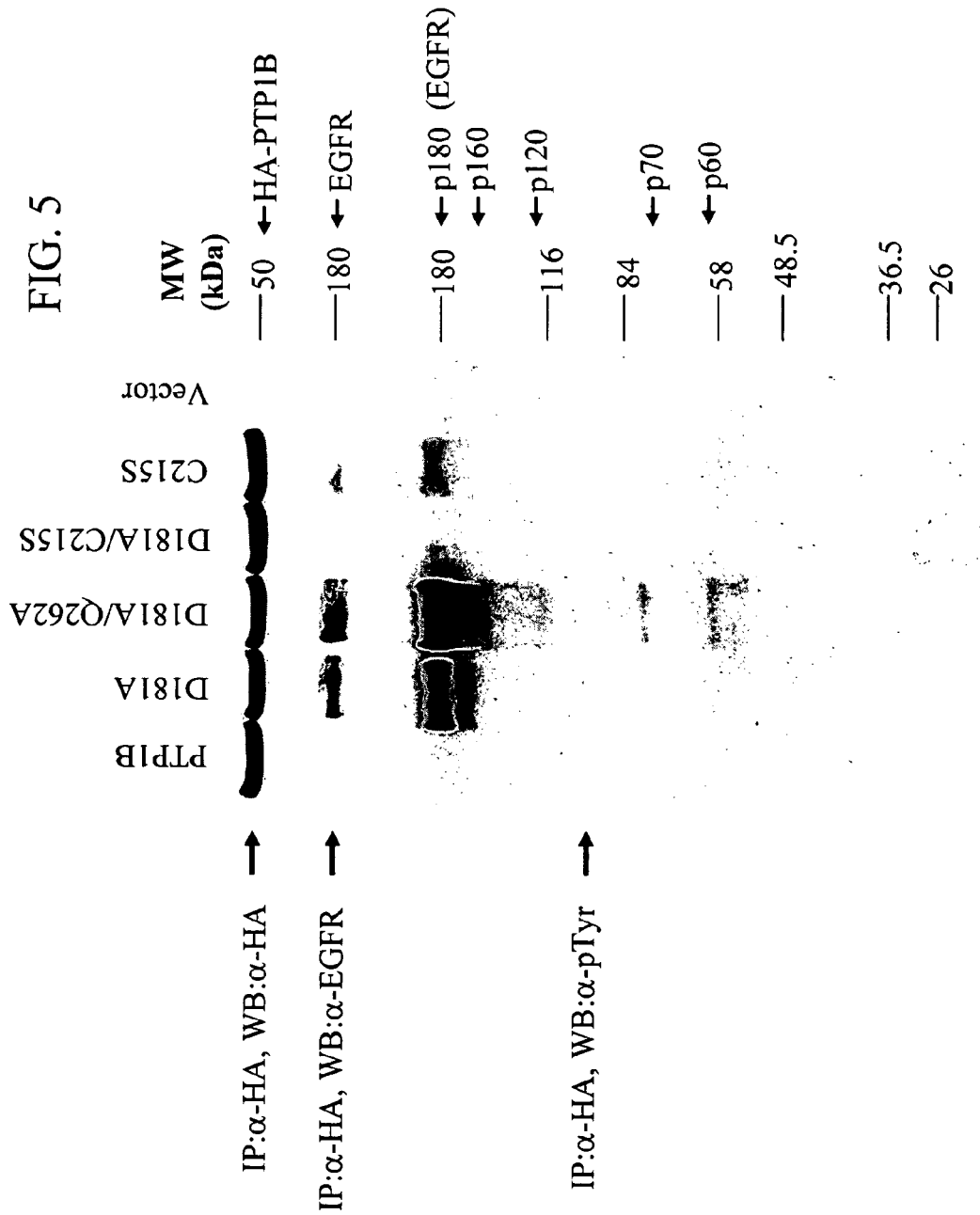
FIG. 5 illustrates immunoprecipitation (IP) and Western blots (WB) of the phospho-EGF receptor, and other less abundant PTP1B substrates, by the PTP1B substrate-trapping mutants. Wild-type PTP1B, D181A, D181A/Q262A, D181A/C215S, C215S, or blank vector (pJ3H) was used to transfect COS1 cells (4 μg plasmid/60 mm dish). The cells were maintained at 37° C. for 44-48 h. Twenty minutes before harvesting the cells, 20 ng/ml EGF was added to each dish. The PTP1B proteins were precipitated from the cell lysates using anti-hemagglutinin (anti-HA) antibody-conjugated agarose beads from the cell lysates (500 μg total protein) at 4° C. overnight. The beads were washed 3 times with the lysis buffer, mixed with 2×SDS sample buffer, and then boiled for 5 min. The immunocomplexes were resolved by SDS-PAGE, and transferred onto a nitrocellulose membrane. The membrane was probed with anti-pTyr HRP-conjugated antibody (lower panel). The membrane was then stripped and reblotted with anti-EGFR rabbit polyclonal antibody (middle panel). Thereafter, the membrane was further stripped, and re-probed with anti-HA HRP conjugate (upper panel).

As shown in FIG. 5, more than 3-fold greater quantities of tyrosine-phosphorylated EGF receptor were co-precipitated with D181A/Q262A than with the D181A mutant. In addition, the amount of EGF receptor protein associated with D181A/Q262A and D181A also corresponded to the level of pTyr in the EGF receptor, suggesting that only the phosphorylated EGF receptor bound to the trapping mutants (FIG. 5). Moreover, the D181A/Q262A double mutant also trapped several novel, less-abundant tyrosine phosphorylated proteins (e.g., P160, P120, P70, and P60; see FIG. 5) that were not visible in either of the D181A or C215S samples. Collectively, then, the inventors have demonstrated, from both substrate protection and substrate pull-down experiments, that D181A/Q262A is a substrate-trapping mutant superior to D181A.

4. Summary

Based on insights from mechanistic studies, the inventors designed several mutant PTP1Bs in order to create substrate-trapping mutants with improved properties over the existing mutants. Kinetic and thermodynamic characterization indicated that PTP1B/D181A/Q262A possesses further decreased catalytic activity and increased substrate-binding affinity than does PTP1B/D181A. These properties suggest that D181A/Q262A would serve as an improved substrate-trapping mutant, as compared with D181A. Indeed, in vivo substrate-trapping experiments indicated that this is the case: D181A/Q262A displays higher affinity for a bona fide PTP1B substrate, the EGF receptor, than does D181A. Further, D181A/Q262A also trapped several novel, less-abundant protein substrates that are missed by both D181A and C215S mutants. Thus, this newly-developed and improved substrate-trapping mutant can be used as a powerful affinity reagent to isolate and purify PTP1B physiological substrates.

Because of the conserved roles of Asp181 and Gln262 in PTP catalysis, and the proximity of these residues to the active site (pTyr pocket), it is unlikely that D181A/Q262A and D181A would exhibit substrate specificity different from that of the wild-type enzyme. Furthermore, given that both Asp181 and Gln262 are invariant among the PTP family, it is predicted this improved substrate-trapping mutant would be applicable to the identification of physiological substrates for all members of the PTP family.

REFERENCES

1. Neel and Tonks, *Curr. Opin. Cell Biol.*, 9:193-204, 1997.
2. Li and Dixon, *Semin. Immunol.*, 12:75-84, 2000.
3. Zhang, Z.-Y., *Curr. Opin. Chem. Biol.*, 5:416-23, 2001.
4. International Human Genome Sequencing Consortium. *Nature*, 409:860-921, 2001.
5. Zhang, Z.-Y., *Crit. Rev. Biochem. & Mol. Biol.*, 33:1-52, 1998.
6. Guan and Dixon, *J. Biol. Chem.*, 266:17026-030, 1991.
7. Cho et al., *J. Amer. Chem. Soc.*, 114:7296-98, 1992.
8. Zhang et al., *Proc. Natl. Acad. Sci. USA*, 91:1624-27, 1994.
9. Hengge et al., *Biochemistry*, 34:13982-87, 1995.
10. Wu and Zhang, *Biochemistry*, 35:5426-34, 1996.
11. Denu et al., *Proc. Natl. Acad. Sci. USA*, 93:2493-98, 1996.
12. Zhang et al., *Biochemistry*, 38:12111-23, 1999.
13. Hoff et al., *J. Am. Chem. Soc.*, 121, 9514-21, 1999.
14. Bliska et al., *J. Exp. Med.*, 176:1625-30, 1992.
15. Sun et al., *Cell*, 75:487-93, 1993.
16. Milarski et al., *J. Biol. Chem.*, 268:23634-39, 1993.
17. Garton et al., *Mol. Cell. Biol.*, 16:6408-18, 1996.
18. Flint et al., *Proc. Natl. Acad. Sci. USA*, 94:1680-85, 1997.
19. Liu et al., *J. Biol. Chem.*, 271:31290-95, 1996.
20. Black and Bliska, *EMBO J.*, 16:2730-44, 1997.
21. Buist et al., *J. Biol. Chem.*, 275:20754-61, 2000.
22. Weng et al., *Genes Cells*, 4:185-96, 1999.
23. Noguchi et al., *J. Biol. Chem.*, 276:15216-24, 2001
24. Zhang et al., *J. Biol. Chem.*, 275:34205-12, 2000.
25. Puius et al., *Proc. Natl. Acad. Sci. USA*, 94:13420-25, 1997.
26. Sarmiento et al., *J. Biol. Chem.*, 273:26368-74, 1998.
27. Zhang and Zhang, *Anal. Biochem.*, 261:139-48, 1998.
28. Zhang et al., *Anal. Biochem.*, 211:7-15, 1993.
29. Wiseman et al., *Anal. Biochem.*, 179:131-37, 1989.
30. Sells and Chernoff, *Gene*, 152:187-89, 1995.
31. Laemmli, U.K., *Nature*, 227:680-85, 1970.
32. Zhang and Wu, *Biochemistry*, 36:1362-69, 1997.
33. Zhang and Dixon, *Biochemistry*, 32:9340-45, 1993.
34. Juszczak et al., *Biochemistry*, 36:2227-36, 1997.
35. Wang et al., *Biochemistry*, 37:15289-99, 1998.
36. Zhao et al., *J. Biol. Chem.*, 273:5484-92, 1998.
37. Jia et al., *Science*, 268:1754-58, 1995.
38. Pannifer et al., *J. Biol. Chem.*, 273:10454-62, 1998.
39. Zhang, Z.-Y., *J. Biol. Chem.*, 270:11199-204, 1995.
40. Fersht, A., *Enzyme Structure and Mechanism*, 2nd ed. (New York: W. H. Freeman & Co., 1985) 104-5.
41. Burke et al., *J. Org. Chem.*, 58:1336-40, 1993.
42. Chen et al., *Biochem. Biophys. Res. Commun.*, 216:976-84, 1995.
43. Scapin et al., *Protein Sci.*, 10:1596-1605, 2001.

All publications mentioned hereinabove are hereby incorporated by reference in their entireties. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. An isolated or recombinant mutant of human protein tyrosine phosphatase 1B (PTP1B), wherein the mutant consists of the human PTP1B with a replacement of the invariant glutamine residue at position 262 of the human PTP1B with an alanine residue and a replacement of the invariant aspartate residue at position 181 of the human PTP1B with an alanine residue, wherein position 262 of the human PTP1B corresponds to amino acid residue number 14 of SEQ ID NO:3; wherein the replacement residues together cause (i) a reduction in catalytic rate ($k_{cat}$) of the enzyme for hydrolysis of the EGFR$^{988-998}$ peptide DADEpYLIPQQG compared to PTP1B without said replacements, mutant D181A, and mutant Q262A, and (ii) an increase in substrate-binding affinity (decrease in $K_d$) of the enzyme for substrate $A_c$-Asp-Ala-Asp-Glu-F$_2$Pmp-Leu-NH$_2$ compared to PTP1B without said replacements, mutant D181A, mutant C215S, and mutant D181A/C215E.

2. A kit for identifying a substrate of a protein tyrosine phosphatase (PTP), the kit comprising:
   (a) the mutant of claim 1; and
   (b) a reagent suitable for detecting binding of the PTP to a candidate substrate.

3. The kit of claim 2, wherein the reagent is an antibody which is linked to a reporter molecule.

* * * * *